US010422488B1

(12) United States Patent
McEllen et al.

(10) Patent No.: US 10,422,488 B1
(45) Date of Patent: Sep. 24, 2019

(54) METHOD AND MODULE FOR CONVERTING A HARP SYSTEM PORTABLE LAMP TO A MULTI-FUNCTION LED LIGHTING SYSTEM

(71) Applicant: MYLIGHT LLC, Georgetown, SC (US)

(72) Inventors: John McEllen, Chagrin Falls, OH (US); L. Lawton Rogers, III, Georgetown, SC (US)

(*) Notice: Subject to any disclaimer, the term of this patent is extended or adjusted under 35 U.S.C. 154(b) by 0 days.

(21) Appl. No.: 16/269,781

(22) Filed: Feb. 7, 2019

(51) Int. Cl.
*F21K 9/90* (2016.01)
*F21V 23/00* (2015.01)
*F21K 9/238* (2016.01)
*F21V 23/06* (2006.01)
*F21V 3/00* (2015.01)
*F21Y 115/10* (2016.01)

(52) U.S. Cl.
CPC ............. *F21K 9/90* (2013.01); *F21K 9/238* (2016.08); *F21V 3/00* (2013.01); *F21V 23/003* (2013.01); *F21V 23/06* (2013.01); *F21Y 2115/10* (2016.08)

(58) Field of Classification Search
CPC ...... F21K 9/238; F21K 9/23–238; F21K 9/90; F21S 6/002; F21S 6/003; F21V 3/00; F21V 23/003; F21V 23/06
USPC ........................................................ 362/417
See application file for complete search history.

(56) References Cited

U.S. PATENT DOCUMENTS

| 6,874,911 B2* | 4/2005 | Yoneda | F21K 9/00 362/294 |
| 9,388,946 B1* | 7/2016 | Stagni | F21K 9/232 |
| 9,777,902 B1* | 10/2017 | Katterheinrich | F21S 6/005 |
| 2011/0163678 A1* | 7/2011 | Shew | F21S 6/002 315/159 |
| 2013/0063935 A1* | 3/2013 | Thrailkill | F21V 29/004 362/231 |
| 2014/0355276 A1* | 12/2014 | Fisher | F21K 9/232 362/382 |
| 2015/0233558 A1* | 8/2015 | Ticktin | F21V 21/22 362/404 |

* cited by examiner

Primary Examiner — Anh T Mai
Assistant Examiner — Michael Chiang
(74) Attorney, Agent, or Firm — L. Lawton Rogers, III

(57) ABSTRACT

A module for manually converting a Harp System Lamp having single female Edison up-socket to a multi-function LED lighting system, the rapid conversion not requiring any modification of the wiring of the conventional lamp and not requiring the use of tools or any special skills, providing significantly more light for the same or less power, providing greater control over the amount and quality of light available, and preserving the aesthetics of the original lamp by retaining the original body, harp and shade. The module expands the area under the shade from which light may be emitted to include space radially outside the harp thus increasing the flexibility as to both the direction and the wavelengths of the light provided by the converted lamp. Methods of making the conversion are disclosed some of which do not require removal of the harp from the lamp being converted.

24 Claims, 4 Drawing Sheets

METHOD AND MODULE FOR CONVERTING A HARP SYSTEM PORTABLE LAMP TO A MULTI-FUNCTION LED LIGHTING SYSTEM

RELATED APPLICATIONS

This application is related to the McEllen et al application Ser. No. 16/268,878 filed Feb. 6, 2019 entitled "Method And Adaptor For Converting A Harp System Portable Lamp From A Single Up-Socket to A Plural Down-Socket LED Lighting System" the contents of which are hereby incorporated by reference herein.

BACKGROUND OF THE INVENTION

The technology exists today to create highly controllable light source variable in brightness, area and color temperature to facilitate the performance of tasks, to set moods, provide area light, display art, and the like. The known prior art light systems occasionally permit dimming and/or the switching between two kinds of light such a incandescent and florescent, but in general lighting systems designed with greater flexibility are expensive custom systems incorporating a large number of widely spaced light sources.

The present invention relates to an advanced multi-function lighting system and more specifically to the conversion of conventional portable table and floor lamps now in service to such a system, i.e., the manual conversion of the single up-socket of a portable lamp with a harp supported shade to an LED lighting system in which the amount and quality of available area and task light is remotely controllable, the conversion preserving the aesthetics of the original lamp by retaining the body and shade of the lamp and accomplished without the need for tools or special skills, without any wiring or structural changes to the lamp.

Harp System Lamp

There are estimated to be over 500 million portable table and floor lamps in service in homes, apartments, offices, hotels, and the like in the United States and Canada.

Lamps are generally bought to provide light, but the selection of the lamp bought is almost entirely architectural, i.e., the lamp actually selected will be purchased on the basis of the overall appearance of the lamp body and its shade. Lamp aesthetics require that the light source be hidden from direct sight by the shade to reduce glare, and that visual "hot spots" on the shade due to proximity to the light source be avoided. This leads almost universally to a single up-socket in which the shade is supported by a harp, the legs of which are in turn supported by a saddle secured at the junction of the lamp body and up-socket. ("Harp System Lamps"). The harp supports the shade in the desired position relative to the lamp body and offers some protection to the shade by limiting the proximity of the shade to the light source. The total amount of light available from such lamps is defined by the choice of bulb the lamp purchaser puts into the one available up-socket.

The typical Harp System Lamp includes an ornamental base from which the electric power cord extends to an electrical receptacle in the wall or floor. The cored ornamental body encloses the electrical wiring of the lamp and extends upwardly from the base to an up-socket for a base-down Edison based bulb.

The saddle is generally located just beneath the up-socket and removably receives the bottom ends of a harp that extends upwardly on both sides of the socket to support the lamp shade. The harp may take various shapes as it rises from the saddle, generally bending radially outward around the up-socket and light source, and then radially inward above the source to the central axis of the lamp to support the shade.

The shade laterally surrounds the up-socket and any bulb mounted therein to diffuse the light and reduce glare, and may be in the form of a cylinder (i.e., a "drum" shade), a truncated cone or pyramid, an oval, a rectangle, or a square. While some light may pass through the shade, the shade is open both at the top to provide area light and at the bottom to provide task light Light Source Limitations In Harp System Lamps Harp System Lamps require a shade to prevent glare and only a very small percentage of the light impinging on the shade passes through it. About 25-50 percent of the lumens emitted by the light source pass out of the opening at the top of the shade to be reflected off the room ceiling to provide indirect area light. About 20% of the total lumens are absorbed within the shade or are transmitted horizontally through the material of the shade.

In general, only about 50% of the total lumens emitted by a base-down bulb exit the bottom of the lamp shade as task light, with about a third of those lumens provided only when the shape and material of the shade directs light impinging on the shade toward the task area. Despite the small proportion of the total lumens available as task light, Harp System Lamps are widely used for a variety of tasks such as to read magazines or newspapers, to do needlework, to play cards, or to work with a computer.

In addition to controlling the amount of light available in Harp System Lamps for area and task lighting, it is highly desirable to control the nature of such light through the use of "smart" devices such as personal communicating devices and systems such as Siri and Alexa. Dimming, color temperature or "mood" and location of the light within a room are lighting functions not available in Harp System Lamps, which typically provide only total lumens adjustment through the use of a three-way up socket and switch in which the number of light sources within a single bulb may be selected.

While various directional lighting sources and associated control circuits are known, there are significant physical restrictions in using such technology in Harp System Lamps. The light source in a Harp System Lamp must be vertically above and derive its power from the single available up-socket, it must fit within the confines of the lamp shade and must avoid interference with the harp, both during and after installation. In addition, there are heat issues that must be addressed when selecting a light source.

Known light sources in Harp System Lamps are also located radially within the harp, and this location limitation materially restricts the number of point sources and the angles at which light can exit the top and bottom openings in the shade from those point sources.

Among the objects of the present invention is the manual conversion of Harp System Lamps to an multi-function LED lighting system which provides control over the nature of the light provided as well as the location thereof, while preserving the aesthetics of the Harp System Lamp by permitting the continued use of the original harp and shade, all without special skills or tools or modifying the original lamp circuitry.

Another object of the present invention is the expansion of the space available for point sources in a Harp System Lamp radially outside the harp to thereby increase the flexibility of the lamp as to the nature and direction of the light emitted therefrom.

While the most important functional criteria in the conversion of Harp System Lamps is light control while preserving the aesthetics of the lamp, the module of the present invention by which a Harp System Lamp is converted to an multi-function LED lighting system is inexpensive to purchase, easily installed by the typical lamp owner without special skills or tools or changes to the wiring of the Harp System Lamp, long lasting and requires very little power in its operation.

Many other objects and advantages will be apparent from the following detailed description of preferred embodiments when read in conjunction with the appended drawings.

THE DRAWINGS

DETAILED DESCRIPTION OF PREFERRED EMBODIMENTS

Figure 4:
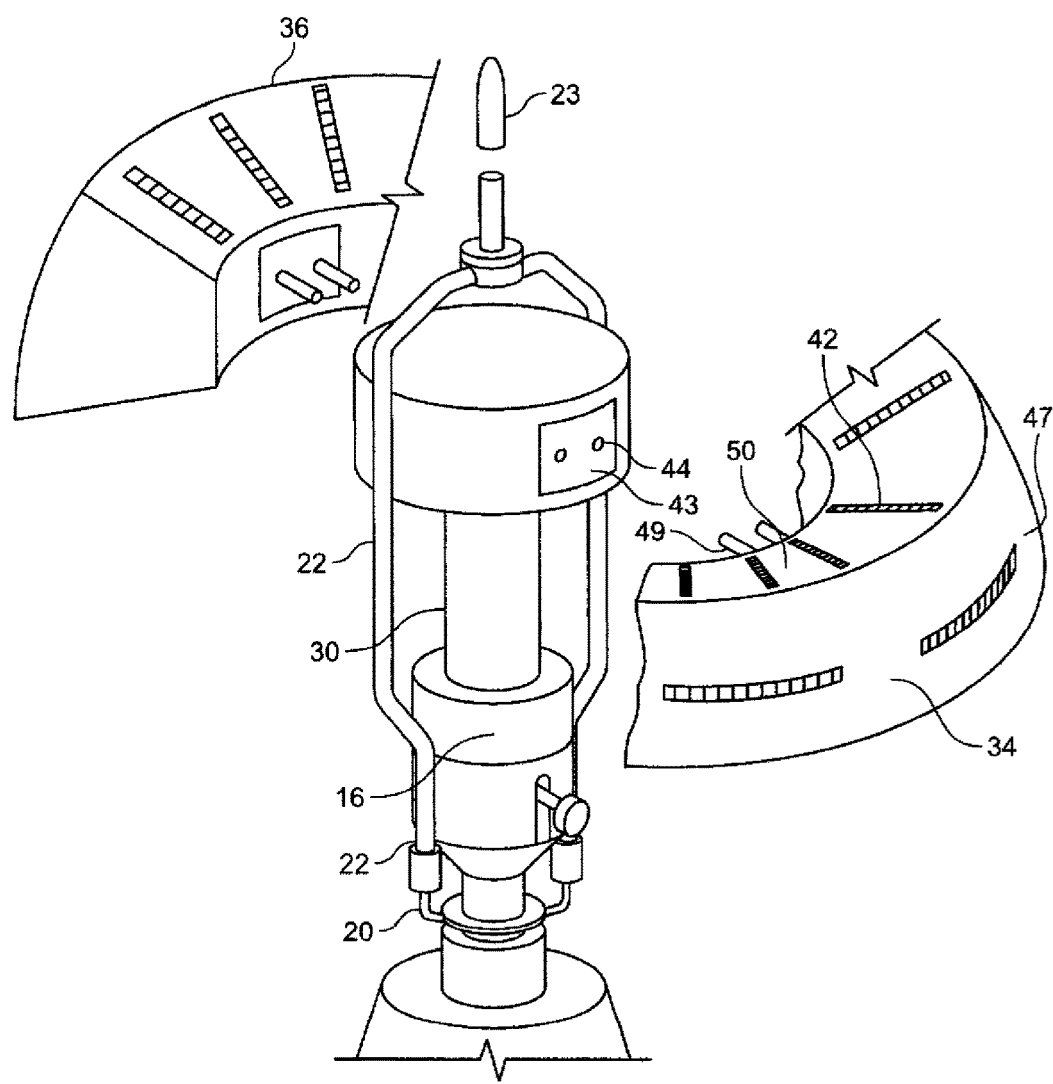
FIG. 4 is a pictorial exploded representation of the column and hub of the adaptor of FIG. 1 installed in a Harp System Lamp with portions of the two light sources shown in FIGS. 2 and 3, showing the assembly thereof.

With reference to the appended drawings of preferred embodiments of the present invention where like numerals have been used for like elements, the single up-socket 16, saddle 20, harp 22, and finial 23 of the Harp System Lamp of FIG. 4 are retained without change. However, the single bulb of the Harp System Lamp is removed from the up-socket 16 and the module of FIGS. 1-4 installed in its place. As shown more clearly in FIG. 4, the adaptor portion of the module preferably includes a central housing or hub 32 carried by a column 30 adjacent the top thereof. Two light sources 34,36 are horizontally connected to the hub 32 of the adaptor to form the assembled module.

Figure 1:
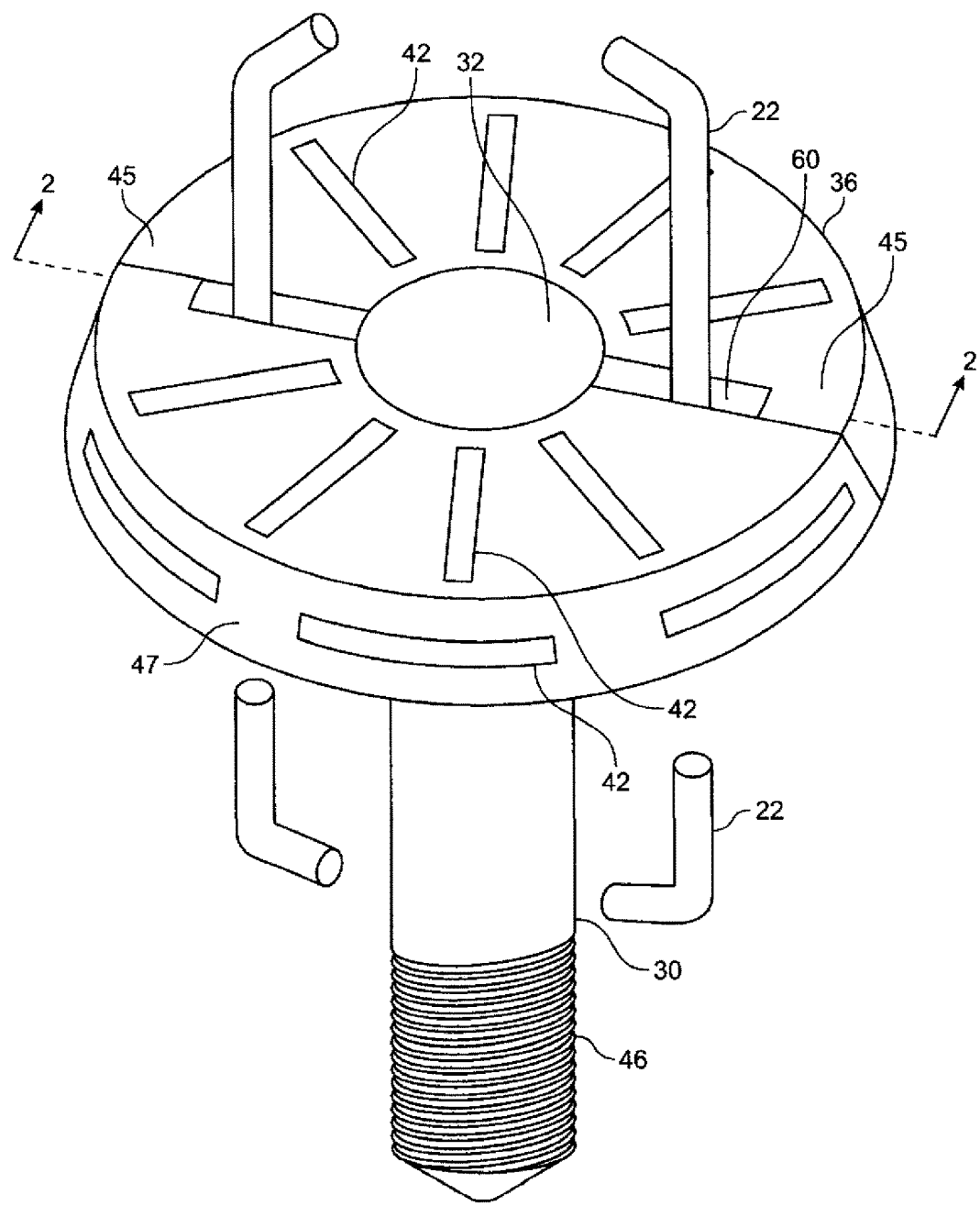
FIG. 1 is a pictorial representation of a separable adaptor and two light source embodiment of the LED lighting system module of the present invention showing an the location of the harp in the slots formed by the two light sources.
Figure 2:
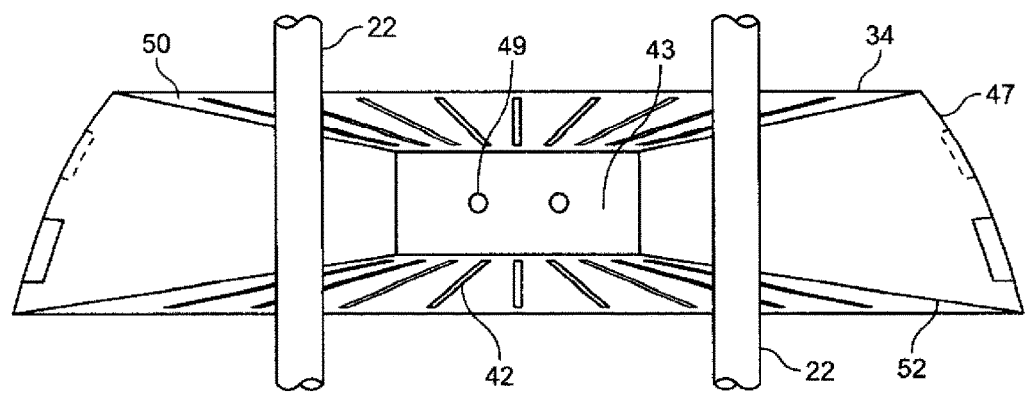
FIG. 2 is a section in elevation of one of two light sources taken through lines 2-2 of FIG. 1.
Figure 3:
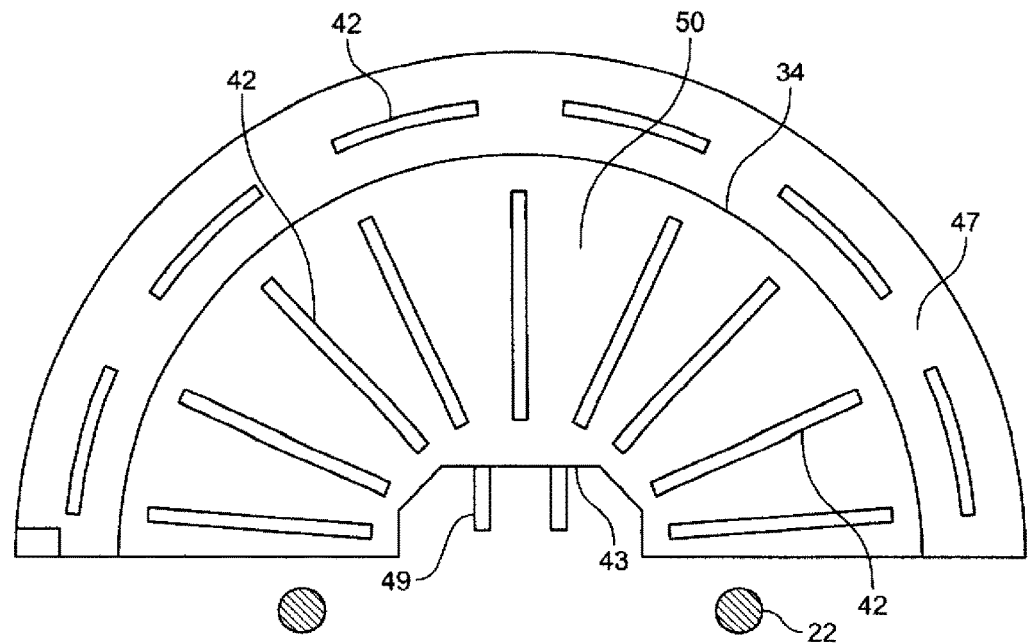
FIG. 3 is a top plan view of the light source of FIG. 2.

As shown in FIG. 1, the lower end of the column 30 terminates in an Edison base 46 that mates with the up-socket 16 of the Harp System Lamp and may be telescoping or otherwise variable in height in any suitable conventional way to adjust the height of the sources carried by the hub 32 with respect to the body of the converted Harp System Lamp.

As suggested by the FIG. 4, the hub 32 may be any d sired shape approximating a square or circle because of the axial symmetry of the lamp, and is shaped to mate with the light sources 34,36. The hub 32 desirably includes opposing flat sections 43 with plural female connectors 44 disposed therein for establishing both a mechanical and electrical connection to the sources 34, 36 described infra in connection with FIGS. 2-4.

In addition to conforming to the shape of the hub 32, the two light sources 34,36 are configured to conform to each other and provide sufficient space between them to accommodate the legs of the harp 22. As shown in FIG. 1, each of the light sources 34,36 may be provided with a horizontally extending projection 45 adjacent the periphery to maintain the separation of the two sources 34,36, and the two sources 34, 36 may be mechanically secured to each other in any suitable conventional manner once connected to the hub 32. By way of example only, a simple hook and eye or hook and pin latch (not shown) may be used as may a more sophisticated plastic snap and release connector at the periphery of the sources 34,36.

As shown in the Figures, the light sources 34, 36 have a plurality of LEDs 42 on the respective upper 50 and lower 52 surfaces thereof and may have additional LEDs 42 on the outward facing peripheral surfaces 47. The LEDs 42 may be mounted on circuit boards in a conventional manner or may be filament LEDs. The LEDs are selected to provide light of different spectra and may be selectively energized through suitable conventional control circuits in the adaptor as discussed infra.

The number and type of the LEDs 42, as well as the location thereof on the surfaces of the sources 34, 36, may also be varied to achieve a desired lighting effect. For example, the surfaces of the sources on which the filaments 42 are carried may have a greater or lesser slope than illustrated, the LEDs may be arranged in horizontal concentric rows rather than radially, the spacing between adjacent LEDs and filaments may be varied, and the LEDs may be arranged so as to create a desired visual design such as a series of diamond shapes.

In the preferred embodiment illustrated, the peripheral edge 47 of the sources 34, 36 is vertically thicker than the center portion which plugs into the hub 32. This provides a generally downwardly concave upper surface 50 and a generally upwardly concave lower surface 52 on which the LEDs 42 may he mounted. The sloping surfaces 50, 52 serve to direct the light from the LEDs 42 toward the holes at the top and bottom of the shade rather than into the internal walls of the shade. A surface slope angle between about 10 degrees and about 12 degrees has been found sufficient for most shades.

The entirety of the hub 32 and the light sources 34, 36 may be contained within a housing (not shown) that serves as a diffusing lens for the LEDs and provides protection therefor, e.g., a diffuser may be disposed over the individual or collective LED bearing surfaces 50, 52 of the two source 34, 36. Alternatively, a liquid may be applied to the surfaces to provide a protective and diffusing coating when dry.

Control of the various LEDs may be accomplished by any suitable control circuit and the design thereof is within the skill of the art. The control circuit is desirably located within the hub 32 and/or the column 30, so that the LEDs of the light sources may be individually controlled to provide the desired distribution of light as well as the spectra thereof.

The selective control of the LED filaments 42 may be accomplished by any suitable conventional means and is well within the state of the art. The number of pins 49 in the connector between the hub 32 and the light sources 34,36 is dependent on the location of the control circuit for the filaments 42 in the light sources 34.36, i.e., if the control circuit is located internally of the sources 34, 36, only power need be supplied through the connector. Alternatively, if the control circuit is located in the column 30 and/or in the hub 32 then additional pins will be required in the connector in the light sources 34,36 to effect the desired degree of LED control.

Wherever located, the control circuit is desirably under remote wireless control from a suitable conventional transmitter (not shown), and controls the conventional application of electrical power from the Edison screw base 46 to the individual LEDs 42 of the sources 34, 36. By varying the type, number and location of the LEDs 42 receiving power, the light from the lamp may be conveniently shifted from area lighting to task lighting, the light dimmed and the color temperature of the light changed, all in a manner well within the skill of the art.

The control circuit and the connections to the filaments has been omitted from the drawings to avoid unnecessary clutter, but the design and operation hereof will be well understood by one skilled in the art, as will the desirability of control of both the intensity and color of the light as well as the direction thereof to the area where the light is desired. Preferably, such control is remote and wireless and may be from a source like a TV remote or an app on a smart phone. In lieu of the on/off control of LEDs of various color, the desired control may be obtained by the use of conventional thin films and/or notch filters, i.e., optical switches, in connection with the coatings described above.

The switch in the socket 16 of the Harp System Lamp may continue to be used as the, on-off control or simply left in the "on" position for exclusively remote control by any smart device.

The rotative orientation of the saddle 20 is fixed relative to the body of the lamp in Harp System Lamps and thus the saddle 20 establishes the plane of the shade supporting harp 22 inserted therein. The rotative orientation of the base 46 becomes fixed relative to the saddle 20, and to the plane of the harp 22, as a result of the base 46 being operatively tightened in the up-socket 16.

The desired flexibility in the lighting provided by the present invention requires the physical location of LEDs both inside and outside of the legs of the harp 22, i.e., that the light source be horizontally wider than the spacing between the legs of the harp 22. Because insertion of the base 46 into the up-socket 16 will not always align the legs in the slots 60 formed by the light sources 34,36, it is necessary to have relative rotation between the base 46 and the slots for the legs of the harp 22 to be located radially internally of the source 34,36. Thus the connectors of the hub 32 must be selectively rotatable relative to the base 46 into an operative position substantially normal to the plane of the harp 22.

As shown in detail in applicant's co-pending application, the hub 32 may be attached to the column 30 by any suitable conventional connection to provide the limited rotation between the column 30 and the connector 44 necessary to avoid interference between the light sources 34,36 and the harp 22. Alternatively, the rotative connection may be located intermediate the height of the column 30 or at the junction of the column 30 and the base 46.

Methods of Conversion

To effect the conversion of a Harp System Lamp from a single up-socket to a multi-function LED lighting system, the finial 23 and shade of the Harp System Lamp are removed providing ready access to the Harp System Lamp socket 16. The saddle 20 and the harp 22 may be left in place. The incandescent, CFL or LED bulb 18 of the Harp System Lamp may then be removed and discarded.

The adaptor portion (i.e., hub 32, column 30 and base 46) of FIG. 4 may then be screwed into the up-socket 16 by clockwise rotation to a mechanically secure and electrically operative position. The hub 32 may then be rotated in a counterclockwise direction relative to the saddle 20 and harp 22 into a position where the connectors 44 of the hub 40 are facing generally normal to the plane of the harp 22.

The two light sources 34, 36 may then be connected to the hub 32. As shown in the figures, there is sufficient space between the facing walls of the two light sources 34, 36 to accommodate the presence of the harp 22. This permits the LED light sources 34, 36 to extend radially outward beyond the harp 22 and greatly enhances the lighting options by increasing the area over which the LEDs 42 may be disposed within the shade.

As a result of the separation of the light source into two halves, and the selective rotatability of the collective light source, the collective light source 34,36 may be installed without removal of the harp 22.

Figure 5:
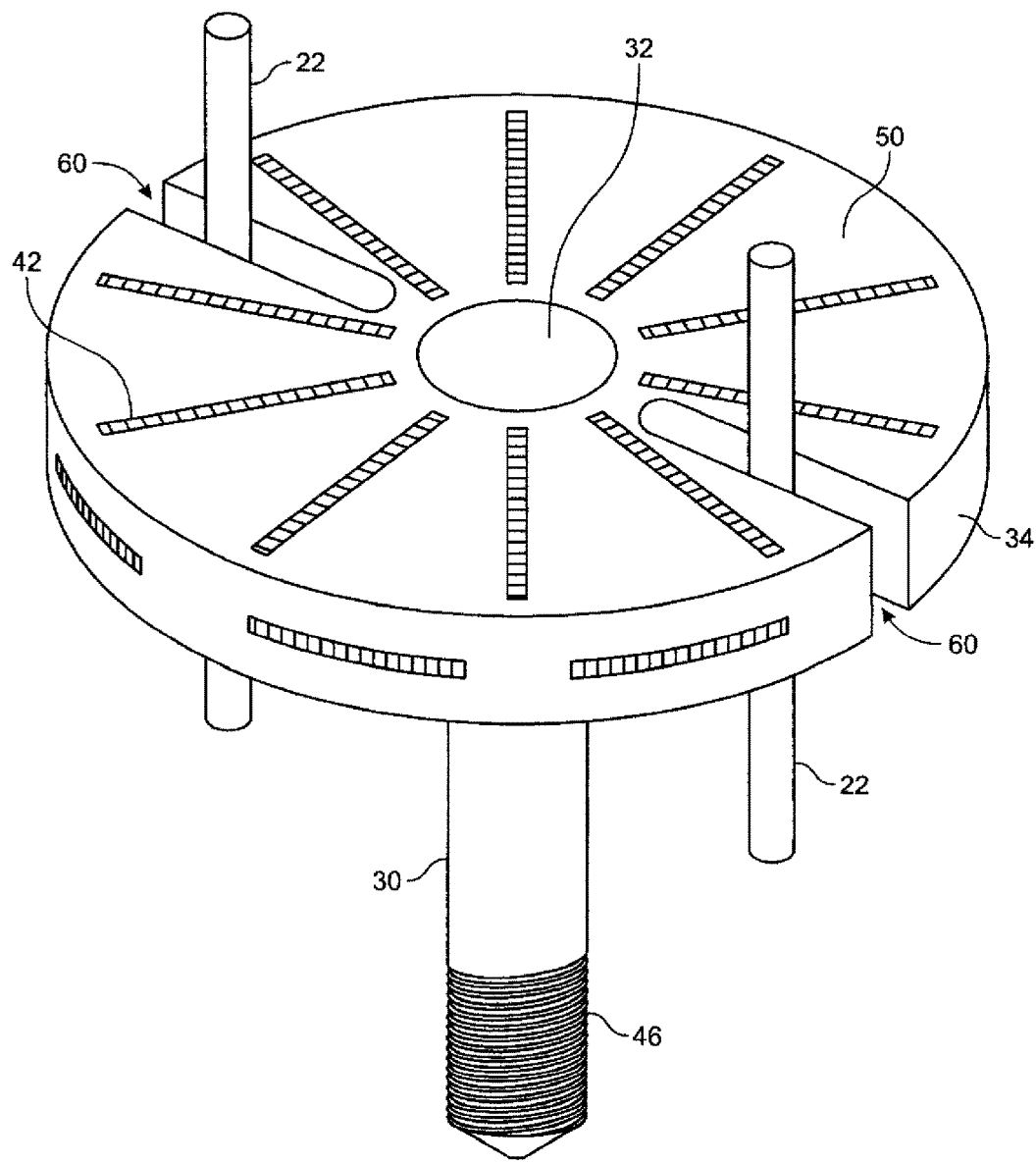
FIG. 5 is a pictorial representation of a one piece adaptor and light source module.

Alternatively, and as shown in FIG. 5, the module may be unitary in constriction with the base 46, column 30, hub 32 and the two light sources 34,36 of FIG. 1 combined into a single unit. Because individual LEDs 42 are located radially within and outside of the harp 22, the harp 22 must be removed from the saddle 20 to rotate module into the up-socket 16, and the harp 22 then positioned into the slots 60 and secured to the saddle 20.

As explained above, the module may be clockwise rotated into a secure mechanical and electrical connection in the up-socket 16, and the slots 60 of the module then rotated counter-clockwise relative to the base 46 into alignment with the saddle 20 and the plane of the harp 22. As in the other embodiments described, such limited counter-clockwise rotation is made possible by the rotator (not shown in FIG. 5). A suitable conventional detent mechanism (not shown) may be used to maintain the rotative position to which the module is thus manually set.

ADVANTAGES AND SCOPE OF INVENTION

While the foregoing is a description of preferred embodiments, many variations and modifications will naturally occur to those of skill in this art from a perusal hereof. The advantages of the present invention are significant, and the invention is not to be limited to the embodiments disclosed, but defined only by the claims when accorded a full range of equivalents.

The conversion of a Harp System to a LED lighting system by installation of the claimed module may be made manually, without special tools. No changes in the electrical circuit of the Harp System Lamp are required and so the Harp System Lamp owner does not have to have special skills to effect the conversion.

Importantly, the aesthetic appearance of the Harp System Lamp, the reason the lamp was purchased, is retained through the use of the same lamp body and shade and the saddle and harp that supports the shade relative to the lamp body.

The large number and location of the LEDs of the light course is made possible by the greatly expanded surface area of the light source. LEDs are inherently directional and thus the selective operation of the LEDs provides great flexibility in controlling the amount and nature of the light provided.

The expansion of the area under the shade from which light may be emitted to include space radially outside the harp greatly increases the angles at which light may exit the top and bottom openings of the shade and thus materially increases the flexibility of the lighting system. The expansion also greatly increases the space available for additional sources with light output in a variety of visible and invisible wavelengths (e.g., ultraviolet to safely and effectively sterilize air.

For example, the lamp may provide only indirect area light, or only direct task light, or any combination thereof. The intensity of light may be dimmed or enhanced as may be required by mature users with naturally diminishing eyesight or a visual disability. The selective operation of LEDs of differing color temperatures gives the user the ability to match the light to the task or mood of the room, e.g., newsprint may require over 200 foot-candles for effortless reading, but only 40 foot-candle level is recommended when the reader toggles between reading material and a video terminal such as a computer screen. The degree of control provided by the LED lighting system of the present invention permits adjustment of the light falling on the screen and diminishes the amount of reflective glare.

The use of filament LEDs with many small LEDs rather then the larger conventional circuit board mounted LEDs serves to diffuse the emitted light by spreading the source of lumens over a greater area and reducing glare and shadows. Spreading the heat source also reduces the need for substantial heat sinks generally required in lumen equivalent LED bulbs, and the corresponding reduction in weight favorably impacts the stability of the lamp. Of course, the combination of LED types may be used where the combination of spot, flood, area, task and other special effects are desired.

All of the control may be achieved remotely through the use of "smart" devices.

It will be apparent that the lack of available space inside the harp for the multi-function light source exists for any lamp using a harp to support the shade, whether or not the harp is in an existing lamp with a single up-socket and is retrofit by the module of the present invention, or in a new lamp in which the up-socket is omitted in the manufacturing process and the light source directly wired to the source of power. Thus the features described above are fully applicable to newly manufactured lamps with harp supported shades without the single conventional up-socket.

What is claimed is:

1. A module for converting (a) a portable lamp having a body, a single up-socket, a saddle carried by the body proximate to the socket, a shade supporting harp carried by the saddle, and a shade supported by the harp to (b) a multi-function LED lighting system, said module comprising:
   a column having:
      (i) a connector adapted to mate with the up-socket of the lamp one end,
      (ii) a light source having a plurality of LEDs spaced from said connector having a maximum horizontal spacing greater than the maximum horizontal spacing between two legs of the harp when inserted in the saddle of the lamp, and
      (iii) a rotator for selectively varying the angle of rotation between said connector and said light source; and
   a circuit internally of said column for applying electrical power from the up-socket of the lamp to said light source.

2. The module of claim 1 wherein said light source includes a control circuit for said LEDs; and
   wherein said control circuit and said LEDs are carried by an integral housing structure.

3. The module of claim 2 wherein said integral housing structure is formed to define two opposing slots radially extending inwardly from the periphery thereof with a width sufficient to receive one of the legs of the harp.

4. The module of claim 1 wherein said light source includes a hub having two bulb connectors and two bulbs; and
   wherein said LEDs are mounted in said two bulbs.

5. The module of claim 4 wherein said two bulbs are configured to cooperatively define two opposing slots radially extending inwardly from the periphery of said source with a width sufficient to receive one of the legs of the harp.

6. The module of claim 5 including means for mechanically connecting said two bulbs when connected to said hub.

7. The module of claim 4 wherein each of said bulbs has an upwardly facing surface including a plurality of said LEDs in said light source for directing light generally toward the top opening defined by the shade.

8. The module of claim 7 wherein said upwardly facing surfaces are upwardly concave.

9. The module of claim 4 wherein each of said bulbs has a downwardly facing surface including a plurality of said LEDs for directing light generally toward the bottom opening defined by the shade.

10. The module of claim 9 wherein said downwardly facing surfaces are downwardly concave.

11. The module of claim 4 wherein the cooperative structure formed by said two bulbs has a vertical dimension which generally increases with the horizontal distance from said hub.

12. The module of claim 1 wherein a plurality of said LEDs are located on a radial periphery of said source to direct light in a general horizontal direction.

13. The module of claim 1 wherein said light source has a maximum horizontal dimension between about 4 inches and about 7.5 inches.

14. The module of claim 1 wherein said LEDs are mounted on circuit boards.

15. The module of claim 1 wherein said LEDs are filament LEDs.

16. The module of claim 1 wherein some of said LEDs are radially inside of the harp and some of said LEDs are radially outside of the harp.

17. The module of claim 1 including a diffuser for said LEDs.

18. The module of claim 1 wherein said column is selectively variable in height.

19. The module of claim 1 wherein said light source includes a control circuit for controlling said LEDs.

20. The module of claim 19 wherein said control circuit is remotely controlled.

21. The module of claim 19 wherein said control circuit controls the brightness and color temperature of said LEDs.

22. The module of claim 19 wherein said control circuit is programable.

23. A method of converting a portable lamp to a multi-function LED lighting system comprising the steps of:
   (a) providing a portable lamp having a body, a single up-socket, a saddle proximate to the socket, a harp carried by the saddle, and a shade supported by the harp;
   (b) removing the shade and harp from the lamp to be converted leaving the saddle and up-socket in place;
   (c) removing any light source installed in the up-socket of the lamp to be converted;
   (d) providing a vertical column having a connector adapted to mate with the up-socket of the lamp on one end and a plural LED light source at the other end, said light source having a maximum horizontal dimension greater than the maximum horizontal spacing between two legs of the harp when inserted in the saddle of the lamp and having two slots extending radially inwardly from the horizontal periphery thereof each configured to permit the passage of a leg of the harp therethrough sufficiently to mate with the saddle;
   (e) operatively installing the vertical column in the up-socket;

(f) rotating the light source relative to the connector to operatively align the slots of the light source with the saddle;
(g) replacing the harp in the saddle;
(h) replacing the shade on the harp.

24. A method of converting a portable lamp to a multi-function LED lighting system comprising the steps of:
(a) providing a portable lamp having a body, a single up-socket, a saddle proximate to the socket, a harp carried by the saddle, and a shade supported by the harp;
(b) removing the shade from the lamp to be converted leaving the saddle, up-socket and harp in place;
(c) removing any light source installed in the up-socket of the lamp to be converted;
(d) providing a vertical column having a connector adapted to mate with the up-socket of the lamp on one end and control hub with two LED light source connectors at the other end, said hub having a maximum horizontal dimension less than the maximum horizontal spacing between two legs of the harp when inserted in the saddle of the lamp;
(e) operatively installing the column in the up-socket;
(f) rotating the hub to align the LED light source connectors generally normal to the saddle;
(g) providing two plural LED light sources each adapted to be operatively connected to the hub, the two light sources having a maximum combined horizontal dimension greater than the maximum horizontal spacing between two legs of the harp when inserted in the saddle of the lamp and the two light sources being configured to provide space for two legs of the harp therebetween;
(h) operatively installing the two light sources in the hub;
(i) installing the harp in the saddle with the legs thereof in the space between the two light sources; and
(j) replacing the shade on the harp.

* * * * *